United States Patent
Hulse et al.

(10) Patent No.: US 8,066,901 B1
(45) Date of Patent: Nov. 29, 2011

(54) AZEOTROPE-LIKE COMPOSITIONS OF TRANS-1,1,1,4,4,4-HEXAFLUORO-2-BUTENE AND WATER

(75) Inventors: Ryan Hulse, Getzville, NY (US); Hang T. Pham, Amherst, NY (US); Rajiv Ratna Singh, Getzville, NY (US)

(73) Assignee: Honeywell International Inc., Morristown, NJ (US)

( * ) Notice: Subject to any disclaimer, the term of this patent is extended or adjusted under 35 U.S.C. 154(b) by 0 days.

(21) Appl. No.: 13/009,198

(22) Filed: Jan. 19, 2011

(51) Int. Cl.
*C09K 5/04* (2006.01)

(52) U.S. Cl. ............................................. 252/67; 203/95

(58) Field of Classification Search ................... 252/67, 252/68; 203/95
See application file for complete search history.

(56) References Cited

U.S. PATENT DOCUMENTS

| 2006/0106263 A1 | 5/2006 | Miller et al. |
| 2009/0204443 A1* | 8/2009 | Tucker et al. ..................... 705/4 |
| 2010/0078585 A1 | 4/2010 | Robin |
| 2010/0163776 A1 | 7/2010 | Robin |

FOREIGN PATENT DOCUMENTS

| WO | 2008008519 A2 | 1/2008 |
| WO | 2009155490 A1 | 12/2009 |

* cited by examiner

*Primary Examiner* — John Hardee
(74) *Attorney, Agent, or Firm* — Bruce O. Bradford

(57) ABSTRACT

Provided are azeotropic and azeotrope-like compositions of trans-1,1,1,4,4,4-hexafluoro-2-butene (HFO-1336mzz(E)) and water. Such azeotropic and azeotrope-like compositions are useful in isolating HFO-1336mzz(E) from impurities during production. Azeotropes of the instant invention are similarly useful in final compositions, such as blowing agent, propellants, refrigerants, diluents for gaseous sterilization and the like.

30 Claims, No Drawings

AZEOTROPE-LIKE COMPOSITIONS OF TRANS-1,1,1,4,4,4-HEXAFLUORO-2-BUTENE AND WATER

FIELD OF THE INVENTION

The present invention pertains to azeotropic and azeotrope-like compositions of trans-1,1,1,4,4,4-heaxafluoro-2-butene (1336mzzm or HFO-1336mzz(E)) and water.

BACKGROUND OF THE INVENTION

Traditionally, chlorofluorocarbons (CFCs) like trichlorofluoromethane and dichlorodifluoromethane have been used as refrigerants, blowing agents and diluents for gaseous sterilization. In recent years, there has been universal concern that completely halogenated chlorofluorocarbons might be detrimental to the Earth's ozone layer. Therefore, stratospherically safer alternatives to these materials are desirable. There is presently a worldwide effort to use fluorine-substituted hydrocarbons which contain fewer or no chlorine substituents. The production of HFCs, i.e. compounds containing only carbon, hydrogen and fluorine, has been the subject of interest to provide environmentally desirable products that could provide a substitute to CFCs. Such compounds are known in the art to be produced by reacting hydrogen fluoride with various hydrochlorocarbon compounds. While HFCs are considered to be much more environmentally advantageous than hydrochlorofluorocarbons (HCFCs) or chlorofluorocarbons (CFCs) because they are not non-ozone depleting, recent data indicates that they may also contribute to greenhouse global warming. Accordingly, alternatives to HFCs, HCFCs, and CFCs are also being explored.

Hydrofluoroolefins ("HFOs") have been proposed as possible replacements. It is generally known that HFOs are best used as a single component fluid or azeotropic mixture, neither of which fractionate on boiling and evaporation. The identification of such compositions is difficult due, at least in part, to the relative unpredictability of azeotrope formation. Therefore, industry is continually seeking new HFO-based mixtures that are acceptable and environmentally safer substitutes for CFCs, HCFCs, and HFCs. This invention satisfies these needs among others.

SUMMARY OF THE INVENTION

The invention provides an azeotropic or azeotrope-like composition of trans-1,1,1,4,4,4-heaxafluoro-2-butene (HFO-1336mzz(E)) and water. The compositions of the instant invention provide environmentally desirable replacements for currently used CFCs, HFCs and HCFCs, since HFO-1336mzz(E) and water have little to no ozone depletion potential. Additionally, a composition containing such an azeotrope exhibits characteristics that make it better than CFCs, HFCs, and HCFCs substitutes, as well as either HFO-1336mzz(E) or water alone.

The invention further provides a composition and method of forming an azeotropic or azeotrope-like composition which comprises a blend of from greater than 0 to about 50 weight percent water and about 50 to less than about 100 weight percent HFO-1336mzz(E), wherein the resulting azeotrope has a boiling point of about 7.0° C.±1° C. at a pressure of about 14.5 psia±2 psia. In further embodiments, the azeotrope has a boiling point of about 7° C. at a pressure of about 14.5 psia, and in even further embodiments, the azeotrope has a boiling point of about 7.0° C. at a pressure of about 14.5 psia.

The instant invention also relates to a method for removing HFO-1336mzz(E) from a mixture containing HFO-1336mzz(E) and at least one impurity by adding water to the mixture in an amount sufficient to form an azeotropic or azeotrope-like composition in accordance with the foregoing weight percentages. This azeotrope is then separated from impurities using standard methods known in the art, such as but not limited to distillation. Impurities may include a halocarbon or hydrogen fluoride, which may or may not be miscible with HFO-1336mzz(E). Examples of halocarbons include, but are not limited to, 1-chloro-3,3,3-trifluoropropene and cis-1,1,1,4,4,4-hexafluoro-2-butene. In further embodiments, the impurities may or may not also form an azeotropic mixture with HFO-1336mzz(E), water or a mixture of HFO-1336mzz(E) and water.

The instant invention also relates to a method for HFO-1336mzz(E) from an azeotropic mixture HFO-1336mzz(E) and water, by separating HFO-1336mzz(E) from the water. Separation methods may include any one or combination of methods known in the art or otherwise discussed herein. For example, HFO-1336mzz(E) may be separated using a liquid-liquid phase separation. In alternative embodiments, HFO-1336mzz(E) may be separated using a drying media (e.g. a molecular sieve, silica alumina or the like). Additional embodiments and advantages of the instant invention will be apparent to one of ordinary skill in the art, based on the disclosure provided herein.

DETAILED DESCRIPTION OF THE INVENTION

In a first aspect of the instant invention, an azeotropic or azeotrope-like composition is provided of HFO-1336mzz(E) and water. This composition provides environmentally desirable replacements for currently used CFCs, HFCs, and HCFCs, since HFO-1336mzz(E) and water have little to no ozone depletion potential. Additionally, a composition containing such an azeotrope exhibits characteristics that make it better than CFC, HFC, and HCFC substitutes, as well as HFO-1336mzz(E) or water alone. In a second aspect of the instant invention, the azeotrope or azeotrope-like composition of HFO-1336mzz(E) and water is used to isolate a purified form of HFO-1336mzz(E).

For purposes of this invention, azeotrope or azeotrope-like mixtures of HFO-1336mzz(E) and water, include those compositions or mixtures that behave like azeotropes. The thermodynamic state of a fluid is defined by its pressure, temperature, liquid composition and vapor composition. For a true azeotropic composition, the liquid composition and vapor phase are essentially equal at a given temperature and pressure range. In practical terms this means that the components cannot be separated during a phase change. For the purpose of this invention, an azeotrope is a liquid mixture that exhibits a maximum or minimum boiling point relative to the boiling points of surrounding mixture compositions. An azeotrope or an azeotrope-like composition is an admixture of two or more different components which, when in liquid form under given pressure, will boil at a substantially constant temperature, which temperature may be higher or lower than the boiling temperatures of the components and which will provide a vapor composition essentially identical to the liquid composition undergoing boiling. For the purpose of this invention, azeotropic compositions are defined to include an azeotrope-like composition which means a composition that behaves like an azeotrope, i.e., has constant-boiling characteristics or a tendency not to fractionate upon boiling or evaporation. Thus, the composition of the vapor formed during boiling or evaporation is the same as or substantially the same as the original liquid composition. Hence, during boiling or evaporation, the liquid composition, if it changes at all, changes only to a minimal or negligible extent. This is in contrast with non-azeotrope-like compositions in which during boiling or evaporation, the liquid composition changes to a substantial degree. Accordingly, the essential features of an azeotrope or an azeotrope-like composition are that at a given pressure, the boiling point of the liquid composition is fixed and that the composition of the vapor above the boiling composition is essentially that of the boiling liquid composition, i.e., essentially no fractionation of the components of the liquid composition takes place. Both the boiling point and the weight percentages of each component of the azeotropic composition may change when the azeotrope or azeotrope-like liquid composition is subjected to boiling at different pressures. Thus, an azeotrope or an azeotrope-like composition may be defined in terms of the relationship that exists between its components or in terms of the compositional ranges of the components or in terms of exact weight percentages of each component of the composition characterized by a fixed boiling point at a specified pressure.

Accordingly, the invention provides azeotrope-like compositions effective amounts of HFO-1336mzz(E) and water. As used herein, "effective amounts" means an amount of each component that, on combination with the other component, results in the formation of an azeotrope-like composition. More specifically, the azeotropic mixture contains from about greater than 0 to about 50 percent water and about 50 to less than about 100 percent HFO-1336mzz(E) based on the weight of the azeotropic or azeotrope-like composition. The azeotropic mixture of the present invention has a boiling point of about 7.0° C.±1° C. at a pressure of about 14.5±2 psia. In further embodiments, azeotropic mixture of the present invention has a boiling point of about 7° C. at a pressure of about 14.5. In an even further embodiment, the azeotrope has a boiling point of from about 7.0° C. at a pressure of from about 14.5 psia.

In a first embodiment, the methods of the instant invention include the steps for generating the HFO-1336mzz(E) and HFO-1336mzz(E)/water azeotrope and for isolating the azeotrope from impurities. The instant methods also include steps for purifying HFO-1336mzz(E) from the azeotropic mixture, which are discussed in greater detail below. This purified azeotrope meets the need in the art for HFO mixtures that have no ozone depletion potential and are negligible contributors to greenhouse global warming and are nonflammable. Such a mixture may be utilized in a wide range of uses such as, but not limited, refrigerants, blowing agents, propellants and diluents for gaseous sterilization. The azeotrope may be provided in combination with other useful additives or ingredients for such purposes.

In a second embodiment, it also may be desirable to separate component parts of the HFO-1336mzz(E) and water azeotrope to a purified form HFO-1336mzz(E). Separation methods may include any method generally known in the art. In one embodiment, for example, the excess water can be removed from the HFO-1336mzz(E) by liquid-liquid phase separation. The remaining water can then be removes from the HFO-1336mzz(E) by distillation and/or a drying media (e.g. molecular sieves silica alumina, and the like). Purified HFO-1336mzz(E) may be used as an end product (i.e. as a refrigerant, blowing agent, propellant, diluents for gaseous sterilization, or the like), or it may be further processed for the production of alternative HFOs or similar compounds. The following non-limiting examples serve to illustrate the invention.

EXAMPLES

Example 1

A glass vacuum insulated vessel fitted with a dry ice cooled condenser is initially charged with HFO-1336mzz(E). Water is then added incrementally and the temperature of the mixture is recorded. The temperature of the mixture reaches a minimum values and then flattens indicating the formation of a heterogeneous azeotrope. The ambient pressure during the measurements was 14.5 psia. The measured temperatures are shown in Table 1.

TABLE 1

Ebulliometer measurements of
HFO-1336mzz(E) and water at 14.5 psi

| Water, wt. % | Temp., ° C. |
|---|---|
| 0.0 | 7.1 |
| 0.5 | 7.0 |
| 2.5 | 7.0 |
| 6.3 | 7.0 |
| 9.9 | 7.0 |
| 16.2 | 7.0 |
| 21.7 | 7.0 |
| 26.5 | 7.0 |
| 30.7 | 7.0 |
| 34.5 | 7.0 |
| 38.3 | 7.0 |
| 41.7 | 7.0 |
| 44.7 | 7.0 |

What is claimed is:

1. An azeotropic or azeotrope-like composition consisting essentially of trans-1,1,1,4,4,4-hexafluoro-2-butene (HFO-1336mzz(E)) and water.

2. An azeotropic or azeotrope-like composition which consists essentially of from about greater than 0 to about 50 weight percent water and from about 50 to less than about 100 weight percent HFO-1336mzz(E), which composition has a boiling point of about 7.0° C.±1° C. at a pressure of about 14.5 psia±2 psia.

3. The composition of claim 2 which consists of water and HFO-1336mzz(E).

4. The composition of claim 2 having a boiling point of about 7.0° C. at a pressure of about 14.5 psia.

5. The composition of claim 2 having a boiling point of about 7° C. at a pressure of about 14.5 psia.

6. A method of forming an azeotropic or azeotrope-like composition comprising forming a blend consisting essentially of from about 0 to about 50 weight percent water and from about 50 to less than about 100 weight percent HFO-1336mzz(E), which composition has a boiling point of about 7.0° C.±1° C. at a pressure of about 14.5 psia±2 psia.

7. The method of claim 6 wherein the composition consists of water and HFO-1336mzz(E).

8. The method of claim 6 having a boiling point of about 7.0° C. at a pressure of about 14.3 psia.

9. The method of claim 6 having a boiling point of about 7° C. at a pressure of about 14.3 psia.

10. A method for removing HFO-1336mzz(E) from a mixture HFO-1336mzz(E) and at least one impurity, comprising adding water to the mixture in an amount sufficient to form an azeotropic or azeotrope-like composition of the HFO-1336mzz(E) and the water, and separating the azeotropic composition from the impurity.

11. The method of claim 10 wherein the impurity does not form an azeotropic mixture with HFO-1336mzz(E), water or a mixture of HFO-1336mzz(E) and water.

12. The method of claim 10 wherein the impurity does form an azeotropic mixture with HFO-1336mzz(E), water or a mixture of HFO-1336mzz(E) and water.

13. The method of claim 10 wherein the impurity comprises a halocarbon.

14. The method of claim 10 wherein the impurity is miscible with HFO-1336mzz(E).

15. The method of claim 10 wherein the impurity comprises HFO-1336mzz(E).

16. The method of claim 10 wherein the impurity comprises cis-1,1,1,4,4,4-hexafluoro-2-butene.

17. The method of claim 10 wherein the impurity is hydrogen fluoride.

18. The method of claim 10 wherein the step of separating the azeotropic composition from the impurity is conducted by distillation.

19. The method of claim 10 wherein the azeotropic composition consists essentially of from about 0 to about 50 weight percent water and from about 50 to less than about 100 weight percent HFO-1336mzz(E).

20. A method for isolating HFO-1336mzz(E) from an azeotropic mixture containing HFO-1336mzz(E) and water, comprising separating HFO-1336mzz(E) from the water.

21. The method of claim 20 wherein HFO-1336mzz(E) is separated from water using a liquid-liquid phase separation.

22. The method of claim 20 wherein HFO-1336mzz(E) is separated from water using a drying media.

23. The method of claim 22 wherein the drying media is a molecular sieve or silica alumina.

24. The method of claim 20 wherein the azeotropic composition consists essentially of from about 0 to about 50 weight percent water and from about 50 to less than about 100 weight percent HFO-1336mzz(E).

25. A method for removing HFO-1336mzz(E) from a mixture containing HFO-1336mzz(E) and at least one impurity, which comprises adding water to the mixture in an amount sufficient to form an azeotropic or azeotrope-like composition of the HFO-1336mzz(E) and the water, separating the azeotropic composition from the impurity; and separating HFO-1336mzz(E) from the water.

26. The method of claim 25 wherein the azeotropic composition consists essentially of from about 0 to about 50 weight percent water and from about 50 to less than about 100 weight percent HFO-1336mzz(E) which composition has a boiling point of about $7.0° C. \pm 1° C.$ at a pressure of about $14.5$ psia$\pm 2$ psia.

27. The method of claim 25 wherein the step of separating the azeotropic composition from the impurity is conducted by distillation.

28. The method of claim 25 wherein HFO-1336mzz(E) is separated from water using a liquid-liquid phase separation.

29. The method of claim 25 wherein HFO-1336mzz(E) is separated from water using a drying media.

30. The method of claim 29 wherein the drying media is a molecular sieve or silica alumina.

* * * * *